United States Patent [19]

Sturrock et al.

[11] Patent Number: 4,628,463

[45] Date of Patent: Dec. 9, 1986

[54] RAPID-SWEEP ELECTROCHEMICAL DETECTOR FOR CHEMICAL ANALYSIS OF FLOW STREAMS

[75] Inventors: Peter E. Sturrock, Doraville; Gerald E. O'Brien, Atlanta, both of Ga.

[73] Assignee: Georgia Tech. Research Institute, Atlanta, Ga.

[21] Appl. No.: 585,429

[22] Filed: Mar. 5, 1984

[51] Int. Cl.[4] .................... G01N 27/46; G06F 15/20; G06F 15/46

[52] U.S. Cl. .................. 364/497; 73/61.1 C; 364/200; 364/550; 340/347 CC

[58] Field of Search .................. 73/61.1 C; 210/635, 210/656; 364/497, 574, 200, 550; 340/347 CC

[56] References Cited

U.S. PATENT DOCUMENTS

| | | | |
|---|---|---|---|
| 4,272,760 | 6/1981 | Prazak et al. | 340/347 CC |
| 4,364,027 | 12/1982 | Murooka | 340/347 CC |
| 4,376,875 | 3/1983 | Beirne | 179/18 AD X |
| 4,472,771 | 9/1984 | Bienvenu et al. | 364/200 |
| 4,476,026 | 10/1984 | Katz et al. | 210/656 |
| 4,476,713 | 10/1984 | Alfredson | 210/656 X |
| 4,496,454 | 1/1985 | Berger | 73/61.1 C X |
| 4,511,659 | 4/1985 | Matson | 73/61.1 C X |
| 4,524,420 | 6/1985 | Glodo et al. | 364/497 |
| 4,532,043 | 7/1985 | Prud'homme et al. | 210/635 |

Primary Examiner—Errol A. Krass
Assistant Examiner—Edward R. Cosimano
Attorney, Agent, or Firm—Newton, Hopkins & Ormsby

[57] ABSTRACT

A system for identification and quantification of electrochemically active compounds in a flow stream involves stepping the electrode potential in a detector rapidly through the range of interest with a square wave superimposed on a staircase signal and recording the current response as functions of step number and sweep number, i.e., as functions of voltage and time. From the recorded data, a three-dimensional graph (potential, time and current) is structured and from which identification and quantification of the electrochemically active compounds is effected with minimum expenditure of time. The system includes a potentiostat controlled by a computer with, however, independent logic control contained in the potentiostat. Provision is also made to compensate automatically for variations in resistance between the cell electrodes.

17 Claims, 11 Drawing Figures

RAPID-SWEEP ELECTROCHEMICAL DETECTOR FOR CHEMICAL ANALYSIS OF FLOW STREAMS

BACKGROUND OF THE INVENTION

It is well known that overlapping chromatographic peaks or other overlapped data obtained from operation of a differential migration apparatus used to analyze a substance whose composition is to be determined provides serious problems. Representative prior art relating to the subject matter to which the present invention relates is as follows:

| | | |
|---|---|---|
| 4,227,988 | Galwey et al. | October 14, 1980 |
| 4,343,767 | Long et al. | August 10, 1982 |
| 4,353,242 | Harris et al. | October 12, 1982 |
| 4,367,041 | Webb, Jr. et al. | January 4, 1983 |

BRIEF SUMMARY OF THE INVENTION

The system according to the present invention is directed to a novel potentiostat which requires a microprocessor for control. No user controls are available at the potentiostat so that all parameters thereof are controlled by the processor including cell voltage generation, current to voltage converter scale factor, positive feedback for IR compensation, timing and operating modes. In addition, the microprocessor can zero the galvanostat, determine the uncompensated cell resistance and control the electrode stand. In spite of the close relationship between the microprocessor and the potentiostat, no time critical operations are required of the processor during data acquisition for pulse polarography. Thus, the microprocessor can do such tasks as saving data files on disc or driving a graphics display during data acquisition.

The purpose of the invention is to obtain voltammograms, with high sensitivity, from a flow stream such as an HPLC, flow injection analysis, or ion chromatography. A detector suitable for these applications must be able to acquire voltammograms at a high repetition rate and with enough points so that the eluted samples are adequately defined on both the potential and time axes. The large volume of data generated at high repetition rates must be stored so that the data can be retrieved and analyzed numerically and suitable graphic figures generated after the run. A visual display of the data during the experiment enables the operator to monitor performance of both the detector and the flow stream. The primary mode of operation is square-wave voltammetry. However, other modes of operation, such a staircase voltammetry, and DC amperometry may be indicated in some cases, and the instrument must be flexible enough to accomodate these alternate modes.

The above requirements dictate a potentiostat controlled by a programmable computer with disc storage and graphics capability. The fundamental questions in designing such an instrument have to do with the distribution of logic capability and the assignment of tasks to the various logic centers. If a single processor is required to handle all of the timing, control, data acquisition, data storage, and data display, it can do so only at a relatively slow rate. It is possible to simplify this by limiting the amount of data to the size of the available memory and by limiting the display to post-run. It is also possible to use a slaved microprocessor to handle the timing, control and data acquisition. However, the approach used in this invention involves the use of a "smart" potentiostat with considerable logic capability, but not including a microprocessor. In addition, a bit-mapped graphics terminal, including a second processor, is used for display. Once an experiment is started with a system of this invention, the computer has only to supply the potentiostat with the next potential value, accept the current value from the potentiostat, and send the latest value of the cell current to the disc controller and graphics terminal. The result is an instrument that can operate with a square-wave of up to 500 Hz until over 125,000 points have been taken.

For rapid pulse-type experiments and solutions of high resistance, such as are often encountered in HPLC, a means of IR compensation is essential. The present invention provides a mechanism whereby the cell resistance can be calculated and compensated automatically.

DETAILED DESCRIPTION OF THE INVENTION

Figure 1:
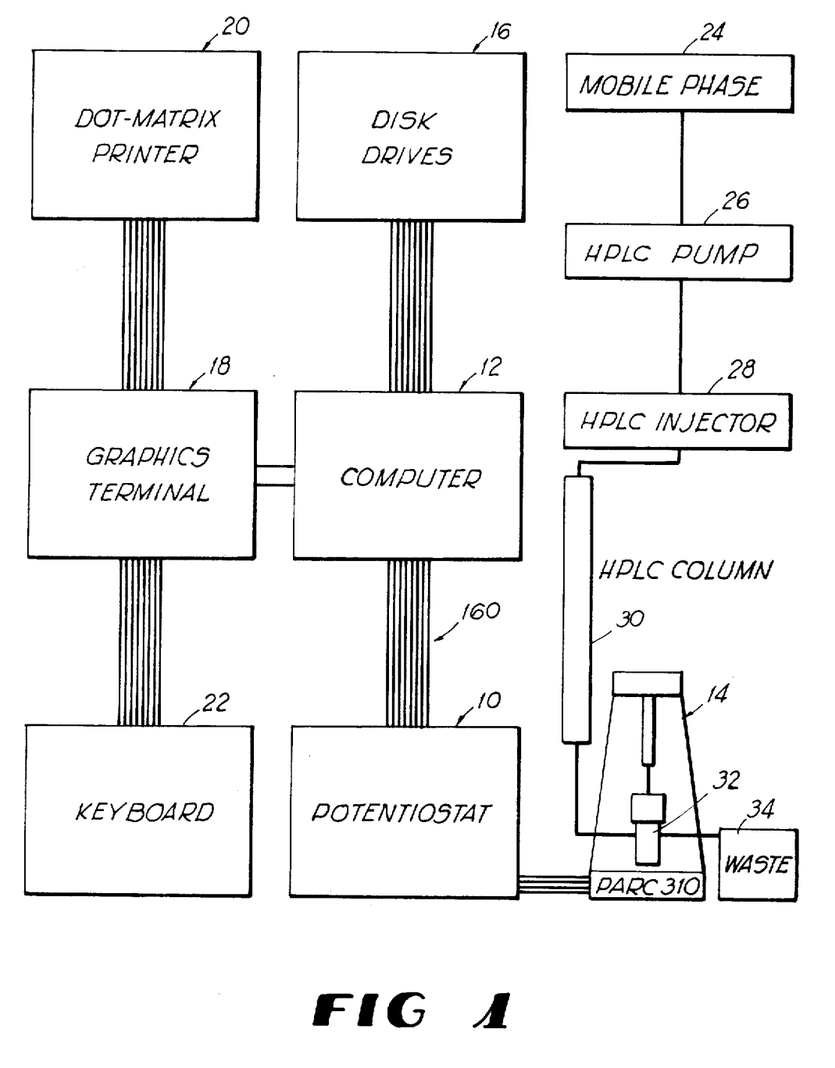
FIG. 1 is a block diagram of a typical system according to this invention.

FIG. 1 illustrates an embodiment of the invention associated with a high pressure liquid chromatography apparatus. The electrochemical detector system of this invention comprises the potentiostat indicated generally by the reference character 10 and associated computer 12 and the electrode stand and flow cell indicated generally by the reference character 14. The computer system consists of a Z80A processor with sixty-four K-bytes of RAM and dual 5.25-inch floppy disc drives 16. The graphics terminal 18 also includes a Z80A processor with sixty-four K-bytes of RAM and the graphics are bit-mapped with six hundred forty points horizontally and four hundred and eighty-one points vertically. Any alpha numerics or graphics can be dumped from the graphics terminal to the IDS Prism 80 dot-matrix printer 20. The instrument-control and data-acquisition programs are written in assembly language while the data processing programs are written in BASIC and FORTRAN IV. To complete the computer system, a keyboard 22 is provided.

The system of this invention as illustrated in FIG. 1 is associated with chromatographic apparatus consisting of the mobile phase source 24, a suitable pulseless pump 26, the injector 28 and the column 30 which discharges through the electrochemical cell 32 and ultimately to waste at 34. The electrode stand and cell 14 is a PARC 310 and the cell 32 contains the usual working electrode, reference electrode and counter electrode.

Figure 3:
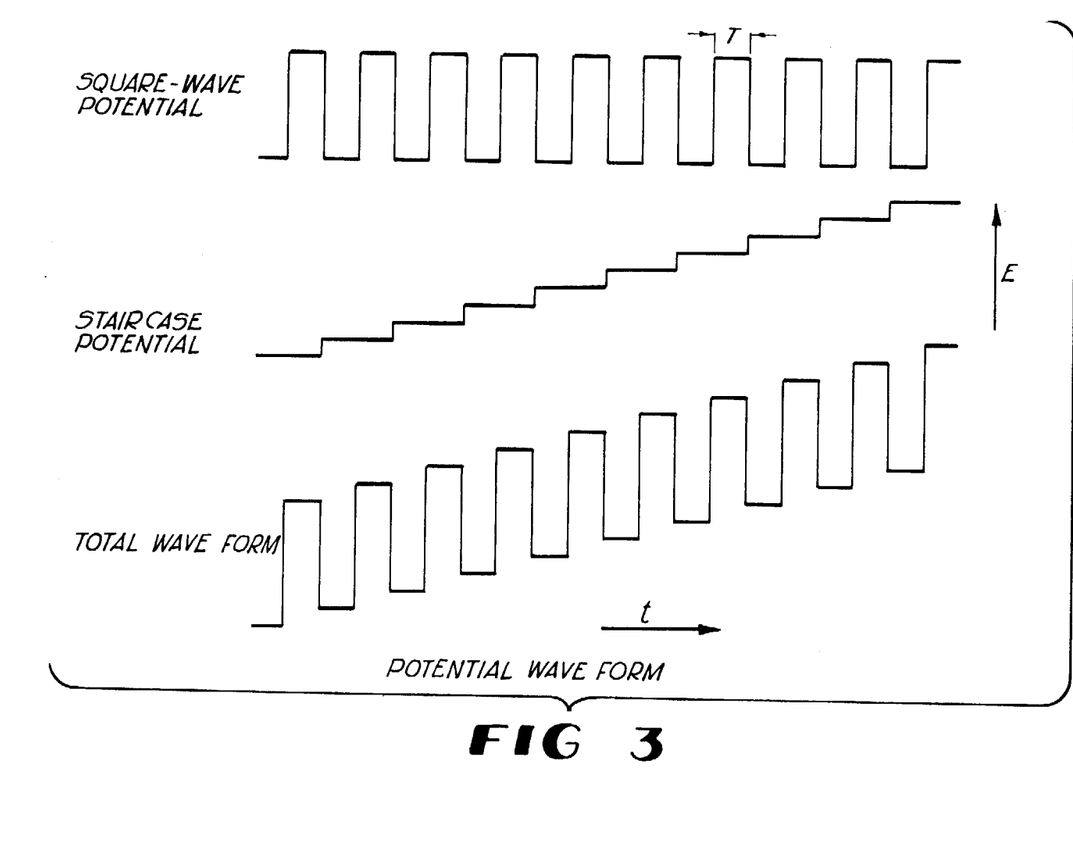
FIG. 3 is a waveform diagram illustrating one of the waveforms used with the invention.
Figure 4:
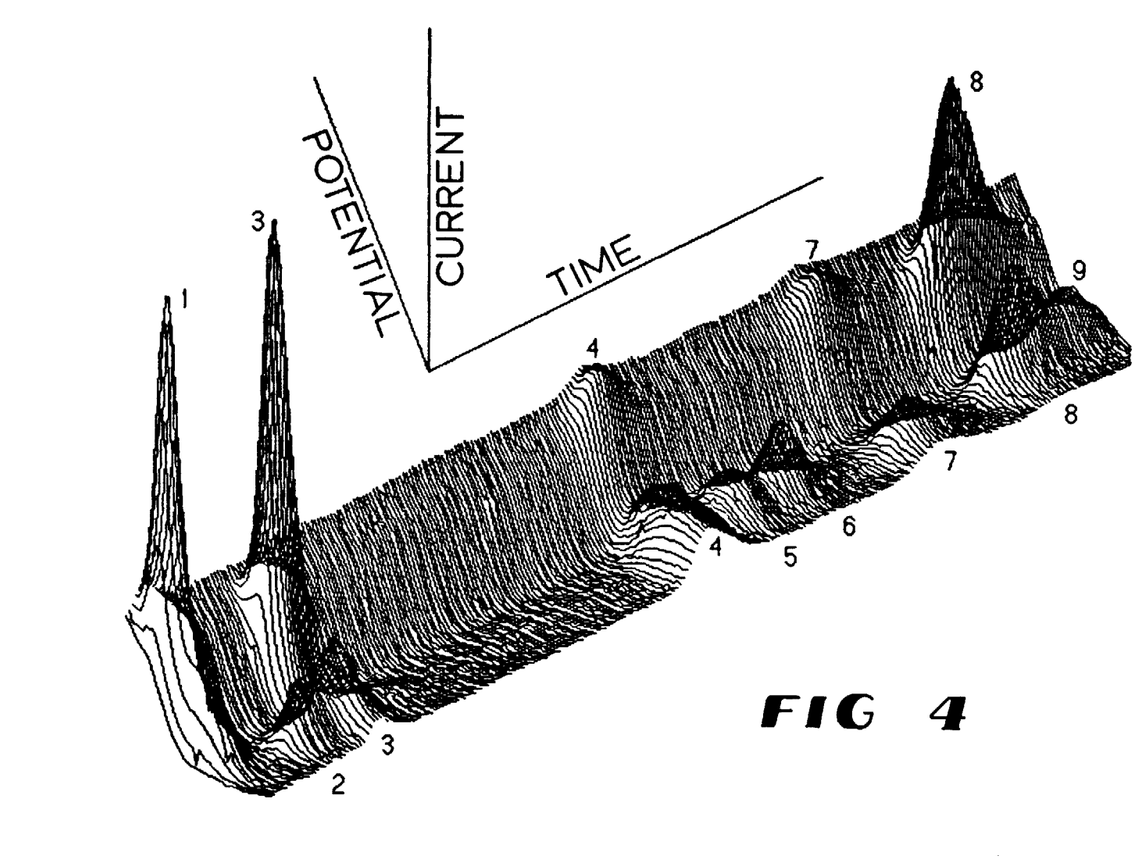
FIG. 4 is a three-dimensional graph illustrating raw data collected by the invention.

FIG. 4 illustrates the type of data which may be gathered, stored, displayed and printed out by the invention. The three-dimensional chromatogram shown illustrates the peaks associated with a mixture of various nitrophenols. The peak 1 was produced by 2,6-dinitrophenol (75 ng); the peak 2 was produced by an unknown impurity; the peaks 3 were produced by 2,4-dinitrophenol (128 ng); the peaks 4 were produced by paranitrophenol (150 ng) and 2,3-dinitrophenol (120 ng); the peak 5 was produced by metanitrophenol (150 ng); the peak 6 was produced by 2,5-dinitrophenol (98 ng); the peaks 7 were produced by 3,4-dinitrophenol (128 ng); the peaks 8 were produced by 2,4-dinitroorthocresol; and the peak 9 was produced by orthonitrophenol (150 ng). For the chromatogram illustrated, the detector was operated with a 30 Hz square wave (top of FIG. 3) of 50 millivolts amplitude on the staircase potential having 10 milivolts per step. The final waveform is shown in the bottom of FIG. 3. Voltammograms were repeated every 2.5 seconds on a fresh mercury drop and in FIG. 4, potentials from $-0.18$ to $-0.66$ volts versus Ag/AgCl with times from 4.4 to 15.6 minutes after sample injections are shown. The peaks 4 represent two components which can be determined individually on the basis of potential. At $-0.18$ volts, the left-hand peak 4 represents pure 2,3-dinitrophenol while the other peak 4, at $-0.66$ volts, represents pure paranitrophenol.

FIG. 4 is an example of the output of the electrochemical detector for flow streams having the swept-potential input illustrated in FIG. 3. The primary advantage of the swept-potential detector is that an additional dimension of information is obtained. The current response as a function of potential can be used to help identify a component and to help resolve two components not completely separated in the column. In addition, the potential for maximum current response is crossed for all components within the potential range of the sweep, thus decreasing the time required to optimize an analytical procedure and allowing the determination of multiple components in one chromatogram, each at its optimum potential. If, as in the present case, the data are stored in a computer file, chromatograms can be displayed for any desired potential within the sweep range, or chromatograms for the summations between desired potentials can be displayed. Thus this detector retains the selectivity of a differential-pulse detector and at the same time is general enough to detect true unknowns.

All parameters for the detector are selected from a menu displayed on the CRT of the terminal 18 and are downloaded from the computer 12 to the potentiostat 10 in digital format. During an experiment, a three-dimensional plot of the data is displayed, as it is acquired, on the upper two-thirds of the CRT while the selected parameters are displayed on the lower third of the CRT. After the experiment, any desired voltammogram or chromatogram can be extracted from the data file, displayed on the CRT, and hard copies made on the printer.

The sensitivity and limit of detection depend on multiple factors. Since the voltammetric peaks of the mononitrophenols are much lower than the first peaks of the dinitrophenols, the mononitrophenols have poorer sensitivities and limits of detection. Column resolution and retention time have obvious effects on peak heights. The data for FIG. 4 were taken with a locally packed column of low plate count. Flow rate is also important. Using the data for FIG. 4, the limit of detection for 2,6-dinitrophenol is estimated to be slightly below one nanogram. An earlier experiment, with a smaller amount injected and different instrument settings, indicated a limit of detection of approximately 250 picograms.

While the application of the swept-potential electrochemical detector is discussed here for HPLC in the reductive mode, the detector is also well suited to oxidation mode detection using a wall-jet detector cell. The detector also finds wide application to flow-injection analysis and ion chromatography.

Figure 2:
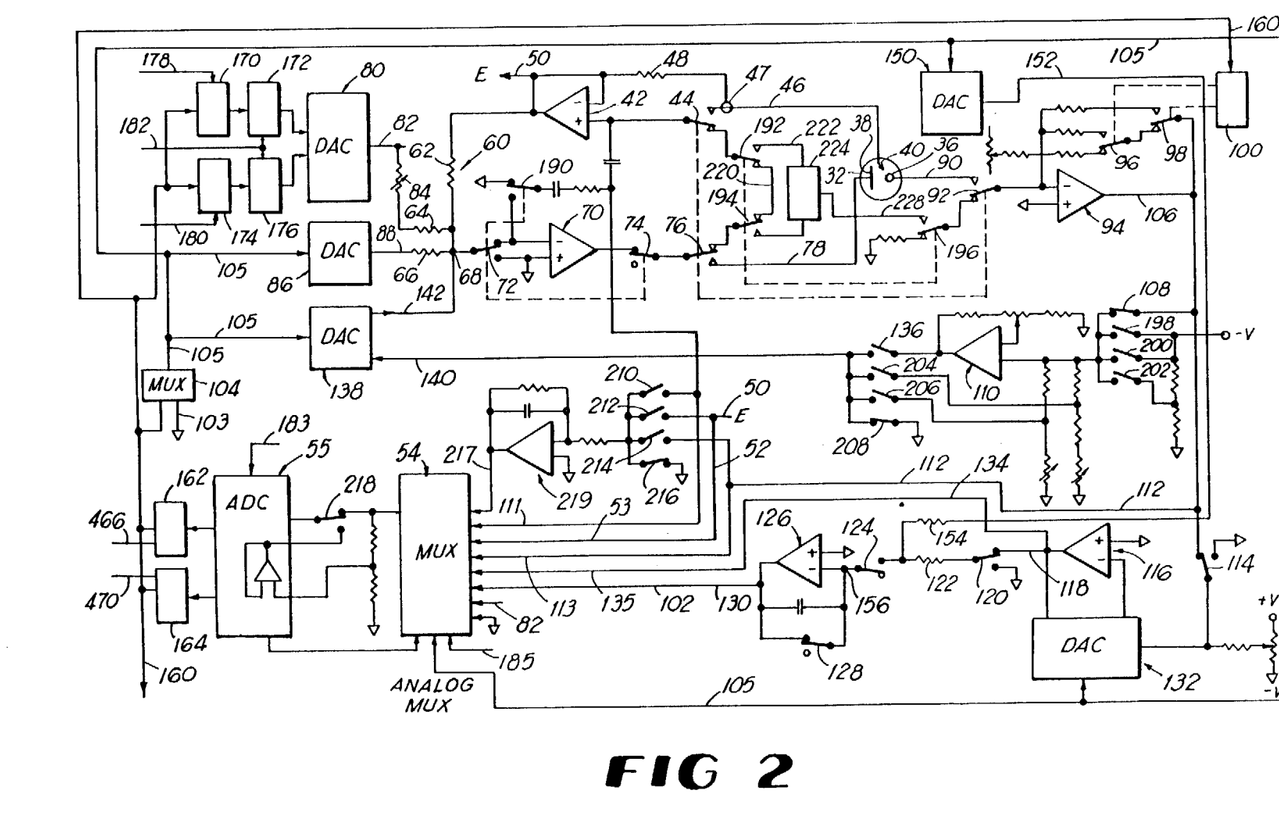
FIG. 2 is a simplified circuit diagram of the potentiostat of this invention.

The basic diagram of the potentiostat 10 or digital polarograph is shown in FIG. 2. The flow cell 32 is illustrated and its working electrode is identified at 36, the counterelectrode at 38 and the reference electrode at 40. Before proceeding to a more detailed description of FIG. 2, it is well to note that the general arrangement is such that the bus 160 between the computer 12 and the potentiostat 10 (see FIG. 1) is in continuous operating connection with the devices 162, 164, 170, 174, 104, and 100 only and is selectively in connection with the devices 86, 138, 150, 132, and 54 through the multiplexing/grounding device 104. The bus 105, then, may be termed an internal bus which may be grounded by the device 104 as indicated at 103.

Figure 5:
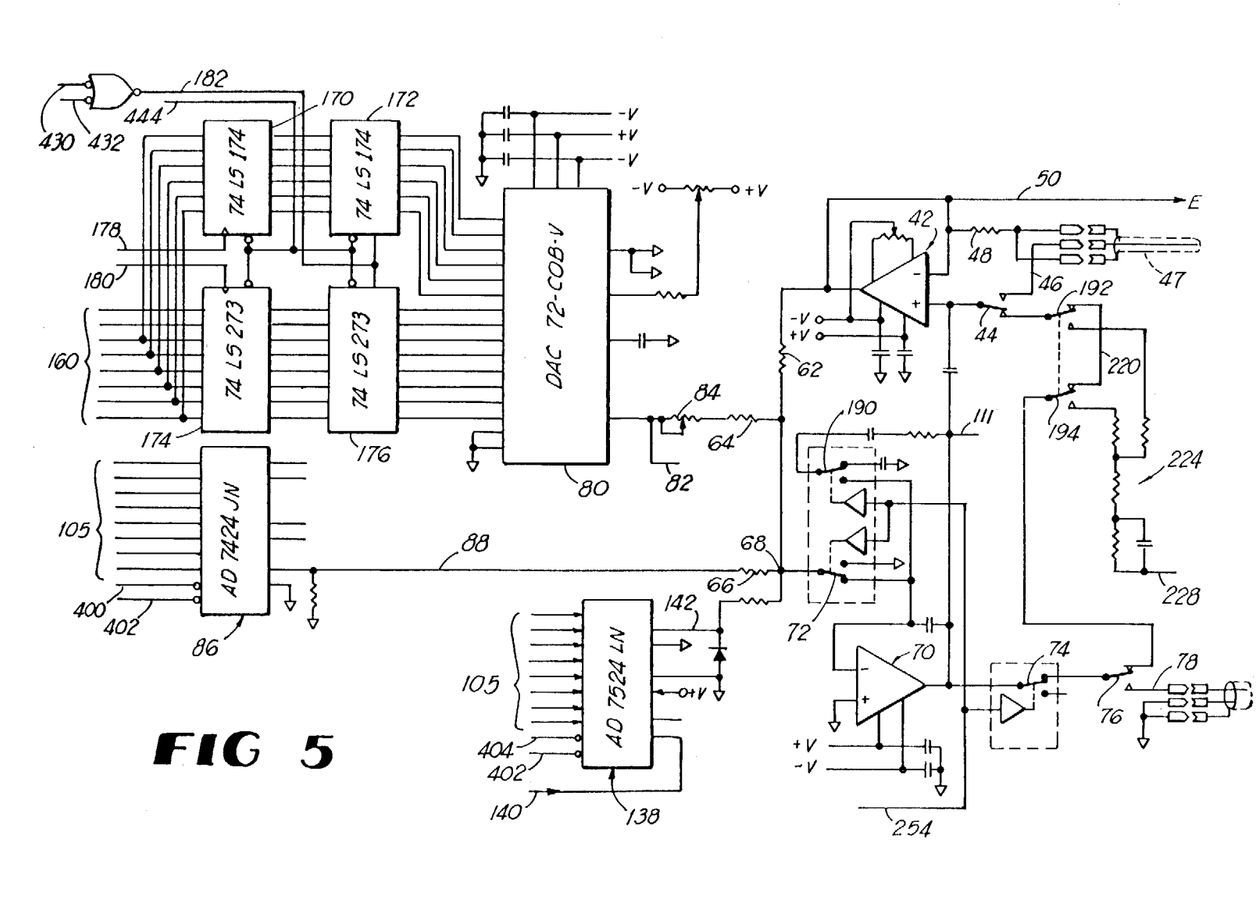
FIGS. 5-10 are diagrams expanding upon the system illustrated generally in FIG. 2.
Figure 6:
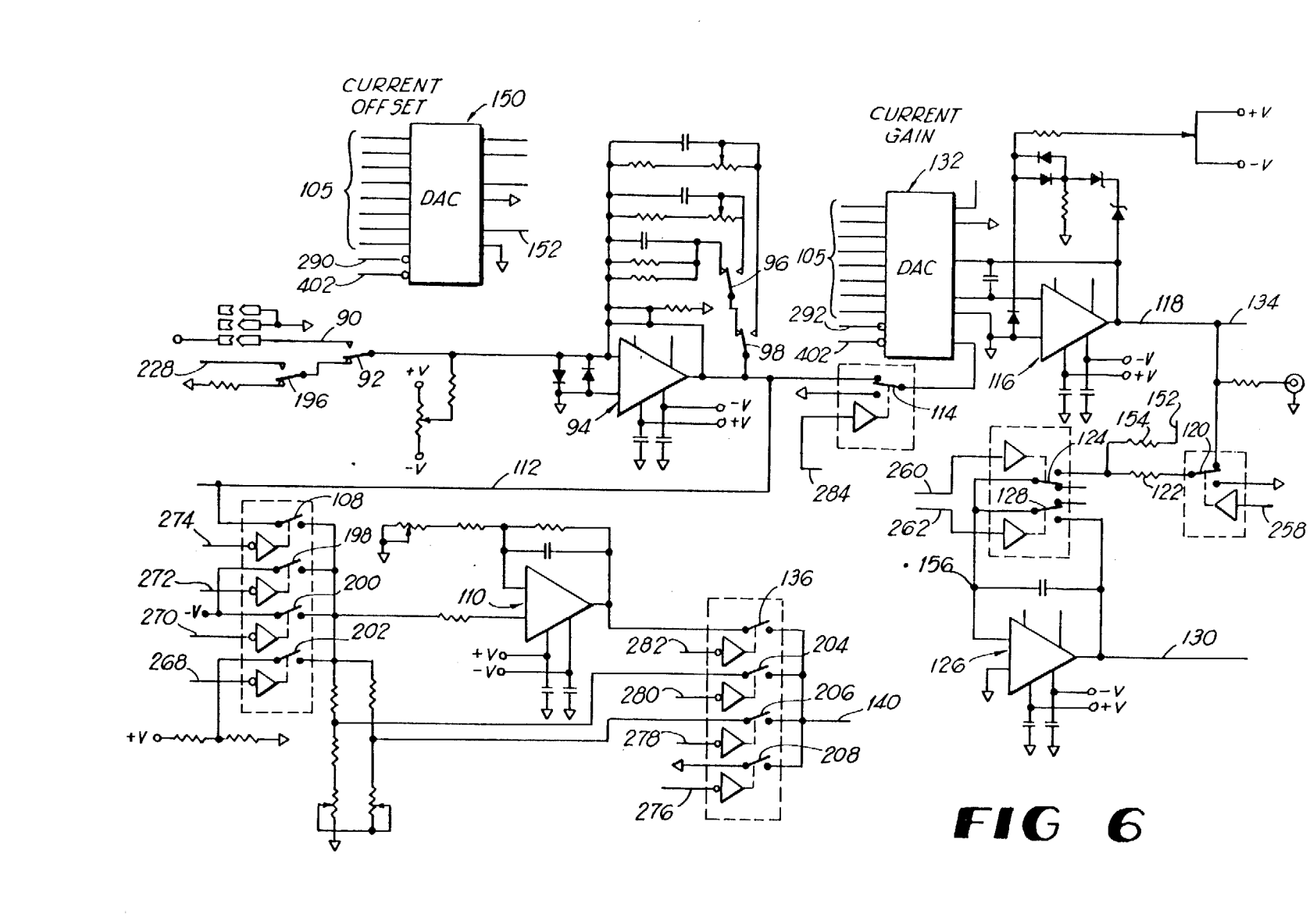
Figure 10:
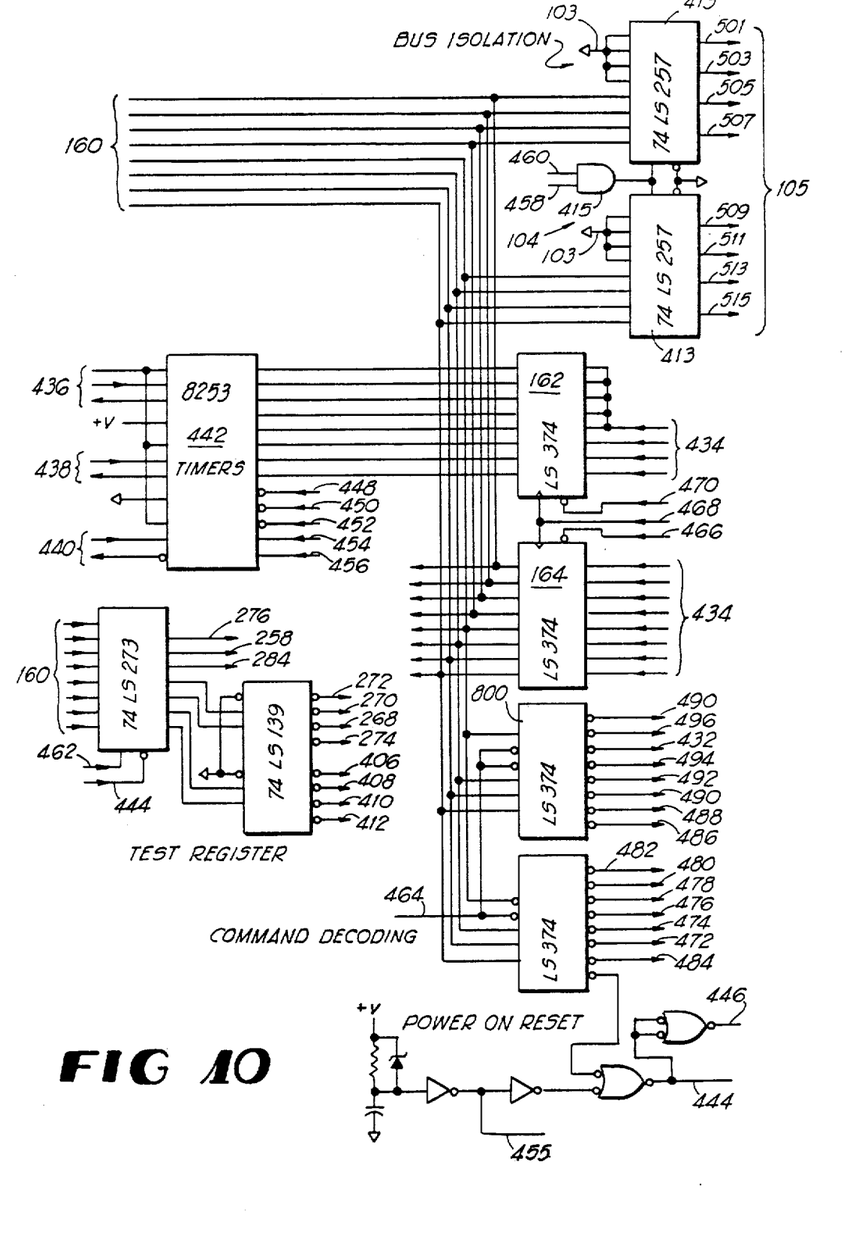

The internal data bus 105 is shown in FIG. 10 and includes the data lines 501, 503, 505, and 507 which are output from the multiplexer 413 at the top and the data lines 509, 511, 513, and 515 which are output from the other multiplexer 413. The internal data bus 105 is used to update the various DAC devices 138, 86, 150, and 132 and to select one of the input lines 217, 111, 53, 113, 135, and 102 of the analog multiplexer to allow such input to be digitized. The entire internal data bus 105 is applied to the cell voltage zero DAC 86 and to the IR compensation DAC 138 as shown in FIG. 5. The entire internal data bus 105 is also applied to the integrating current offset or bucking DAC 150 and to the current scale factor DAC 132 as shown in FIG. 6. Also, the internal data bus lines 509, 511, 513, and 515 are applied to the analog multiplexer 54 for the purpose above stated.

The output from the potentiostat is from the latches 162 and 164 but, as will be seen later, the data outputs back to the computer 12 over the bus 160 is under timing control logic within the potentiostat 10. The internal bus 105 is grounded during data acquisition (i.e., during operation) and may be set for connection to the active data bus 160 only during those periods of time between data acquisition. This is an important feature of the invention because the accuracy of the analog signals being measured and output to the computer through the devices 162, 164 could otherwise be degraded by digital signals present on the bus 160.

Another important feature, detailed later, is the fact that the timing control signals to effect the required logic are generated by the potentiostat itself. These timing signals are illustrated in part in FIG. 2 as being applied over the conductor 182 to update the voltage generating device 80 and as being applied over the conductors 466 and 470 to control the data output to the bus 160.

During operation, the operational amplifier 42 operates as a voltage follower and for this purpose has its non-inverting input connected through the switch 44 to the conductor 46 connected to the reference electrode 40, the inverting input of the operational amplifier 42 being connected to its output. A shield 47 for the conductor 46 is connected to the output through the resistor 48. The output of the amplifier 42 provides the voltage output E at 50 which is connected through the conductor 52 to one channel 53 of the analog multiplexer indicated generally by the reference character 54. The output at the operational amplifier 42 is also connected to an adding circuit indicated generally by the reference character 60 and which includes the resistors 62, 64 and 66 to provide the summing point 68 for the operational amplifier 70. Normally, this summing point 68 is connected to the inverting input of the amplifier 70 through the switch 72 and its output is connected through the switch 74 and also the switch 76 to the conductor 78 connected to the counter electrode 38 of the cell 32.

The digital to analog converter (DAC) 80 is the cell voltage generator and provides the requisite analog voltage output at 82 which is applied through the calibrating resistor 84 and the aforementioned resistors 64 to the summing point 68, as shown. A further input to the summing point 68 is from the digital to analog converter 86 having an analog voltage output at 88 through the resistor 66 to the summing point for the purpose of cell voltage zeroing.

The analog current output of the cell 32 at the conductor 90 is normally connected through the switch 92 to the inverting input of the current to voltage converter amplifier indicated generally by the reference character 94. The operational amplifier 94 has three gain settings controlled by the switches 96 and 98 which, in turn, are controlled through the latch 100 by the bus 160, the appropriate signals being supplied prior to data acquistion. The analog current output at 106 is applied, through the switch 108 to the scale factor correction network including operational amplifier 110, over the conductor 112 to a channel of the multiplexer 54, and through the switch 114 to the inverting input of the operational amplifier 116.

The output at 118 of the amplifier 116 is connected normally to the switch 120 and the resistor 122 through the switch 124 to the inverting input of the integrating amplifier 126. The switch 124 is the enabling switch for the amplifier 126 and the switch 128 is the reset switch for this integrator. The output of the integrator at 130 is applied to another channel 102 of the multiplexer 54.

The digital to analog converter 132 is used to set the gain of the amplifier 116 prior to data acquisition, the gain being selectable in a binary sequence from 1 to 256, with the selectable relative gain of the two amplifiers 94 and 116 being in a binary sequence from 1 to 16,384 during which the absolute sensitivity ranges from 1.638 ma to 0.10 μa per volt. These values are augmented by the gated integrator 126.

The output of the amplifier 116 is connected over the conductor 134 to another channel 135 of the multiplexer 54, as shown.

It should be noted that the output of the scale factor correction network is connected through the switches 204, 206, or 136 to the input of the digital to analog converter 138 which selects a value of resistance between its input 140 and its output 142 which cotrols the current applied to the summing point 68 as positive feedback in order to compensate for high internal resistance within the cell 32. For rapid pulse-type experiments in solutions of high resistance, such as often encountered in HPLC, a means of IR compensation is essential and this adjustment or compensation should be done automatically by the system prior to data acquisition. Therefore, the system of this invention requires the capability to measure the actual cell resistance and set the IR compensation accordingly. A possible method is to use measurements of current versus time following a potential pulse in a region with no Faradaic current and the system of this invention can indeed be programmed to use this method. However, this invention uses an alternate method in which a potential pulse is made to a region where a Faradaic current will flow. The current and potential are measured at a set time after the potential pulse and then the current is interrupted and the potential measured again. The cell resistance is calculated by the computer 12 from these three measurements during a test and the DAC 138 is properly set, through the internal bus 105 so that during subsequent data acquisition, the proper offset is made to the summing point 68.

At this point, it may be well to note that there are various modes of operation of the potentiostat. As noted earlier, during any data acquisition period, the internal bus 105 is grounded or isolated from the sensitive analog circuitry so as not to interfere with accuracy of measurements. The control logic circuitry (FIG. 8) conditions the potentiostat for the desired mode of operation, under command from the computer 12, during which various of the switches shown as mechanical devices in FIG. 2 are set to the desired positions. During these commands, the device 104 must connect the internal bus 105 to the bus 160 and greater detail will appear hereinafter from a description of FIGS. 8-10.

The digital to analog converter 150 is provided to achieve current offset at the integrator 126. For this purpose, its output at the conductor 152 is connected through the resistor 154 and the switch 124 to the summing point 156 of the integrator amplifier 126.

To complete the general description of the embodiment shown in FIG. 2, it should be noted that the two devices 162 and 164 are each an 8-bit latch whereas the previously mentioned device 104 is an 8-bit multiplexer which is also operative to isolate the internal bus 105 as shown in FIG. 10. The 8-bit DAC 138 and the 8-bit DAC 86 respectively control IR compensation and offset of the amplifiers 42 and 70. There are two 6-bit latches 170 and 172 and two 8-bit latches 174 and 176 to provide input to the 14-bit DAC 80. An internal timing signal at the line 178 controls the latch 170 whereas an internal timing signal at the line 180 controls the latch 174 and an internal timing signal at the line 182 controls the two latches 172 and 176 to provide an input to the DAC 80. An internal timing signal 183 controls the analog to digital converter 55 and an internal timing signal 185 controls the analog multiplexer 54. The 2-bit latch device 100 controls the two switches 96 and 98 as indicated by the dashed lines and there are, in addition to the switches already mentioned, the further switches 190, 192, 194, 196, 198, 200, 202, 204, 206, 208, 210, 212, 214, 216, and 218. It is to be noted that the switches 72, 74 and 190 are operated simultaneously as indicated by the dashed lines, that the switches 44, 76 and 92 are ganged together as noted by the dashed line and that the switches 192, 194 and 196 are also ganged together as indicated by the dashed line. The switches 72, 74 and 190 are the current interrupt switches which are under control of the computer 12. The switches 192, 194 and 196 are standby and test switches. During the standby mode, the two switches 192 and 194 connect together in a common connector 220, the position shown in FIG. 2. In the test mode, the switch 192 connects the non-inverting input of the amplifier 42 to the conductor 222 associated with the reference electrode of the dummy cell 224. At the same time, the switch 196 in the standby mode connects the input to the amplifier 94 to ground as in the position shown and in the test mode it connects the amplifier 94 to the working electrode conductor 228. In other words, the standby position of the switch 92 is as shown in FIG. 2 wherein the inverting input of the amplifier 94 can either be connected to ground or to the output of the dummy cell 224 at the conductor 228. During normal operation, however, the switch 92 is in a position to connect the inverting input of the amplifier 94 to the working electrode conductor 90 of the cell 32. The operational amplifier 219 has a gain of sixteen and is used in test mode to obtain very sensitive measurements of various portions of the potentiostat in order to allow proper setting of the various devices 86, 138, and 150. For convenience, the remaining channels to the device 54 are designated 82, 111 and 113.

Referring at this time more particularly to FIG. 5 wherein a portion of the circuit of FIG. 2 is shown and expanded upon, it will be appreciated that the internal data bus 105 is shown as a group of eight conductors. Likewise eight conductors represent the data bus 160. The previously mentioned signals at the lines 178, 180, and 182 receive internally generated signals which are applied to effect the requisite timing of the potentiostat. FIG. 5 also shows that the internally generated signal at the conductor 444 is utilized simultaneously to clear all of the latches 170, 172, 174 and 176. The signal at the line 180 effects loading of the digital data into the register 174 and this is the first operation in the timing sequence described hereinafter whereas the signal at 178 effects loading of the register 170, the second in the timing series. Thereafter, the signal at 182 loads the data from the register 170 and 174 respectively into 172 and 176 for access by the DAC 80. FIG. 5 also illustrates a further conductor 254 which receives an internally generated signal to actuate the switch 74 as well as the two switches 72 and 190.

In FIG. 6, additional internally generated signals are present at 258, 260, 262, 268, 270, 272, 274, 276, 278, 280, 282, and 284 for controlling various of the switches as will hereinafter be more particularly described. Further, the device 150 receives two signals at the conductors 290 and 402 and the device 132 receives signals of the same nature at the conductors 402 and 292 as hereinafter more particularly described.

FIG. 5 also shows internally generated signals at the conductors 400 and 402 which are applied to the device 86 to allow update of its control function for cell voltage zeroing. Similarly, the internal signals that the conductors 402 and 404 control the update of the device 138 for IR compensation. It will be understood that the signal at the conductors 402 is that which controls writing of the update into the two DAC devices 86 and 138, whereas the signals at the conductors 404 control respectively the selection of each device. Before proceeding to the origins of the various control signals, a brief description of FIGS. 6 and 7 will be given.

At the upper left hand corner of FIG. 6, the DAC device 150 produces its output at 152 applied to the summing point 156 as previously mentioned. The updating of the device 150 is controlled by internally generated signals applied to the conductors 290 and 402 to vary the output in the conductor 152. Similarly, control of the update to the DAC 132 is effected at the conductors 292 and 402. In FIG. 6, further control signal conductors carry signals for controlling some of the switches illustrated in FIG. 6 are indicated by the following reference characters: 258, 260, 262, 268, 270, 272, 274, 276, 278, 280, 282 and 284. Without yet going into the details of the generation of the signals at the various conductors, it can be mentioned that the signal at the conductor 258 controls testing of the integrating operational amplifier 126; the signal at the conductor 260 enables the integrator amplifier 126 whereas the signal at the conductor 262 resets the integrator; the signal at the conductor 268 sets its switch 202 for a first test sequence, whereas the signal at the conductor 270 and the signal at the conductor 272 respectively set their switches for subsequent tests in the series; the signal at the conductor 274 sets the switch 108 to the normally closed position when the test sequence is over; and the signals at the various conductors 276, 278, 280 and 282 are used to set IR compensation.

Figure 7:
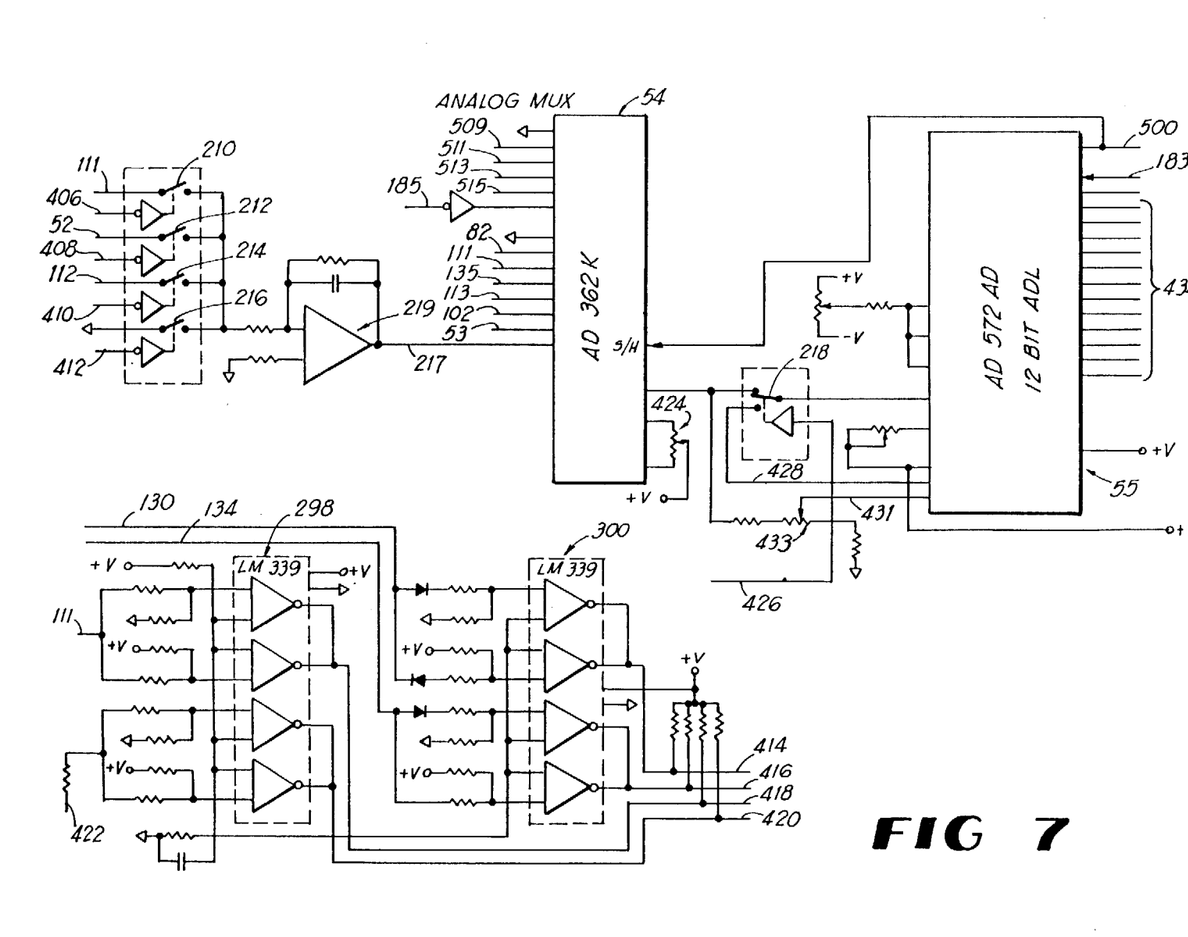

In FIG. 7, three further conductors for controlling the switches 210, 212, 214 and 216 are illustrated respectively by the reference characters 406, 408, 410 and 412 and these signals respectively select various of the inputs to the amplifier 219 for application to the device 54. Normally, the switch 216 is closed so as to zero the output of the amplifier 219. FIG. 7 additionally shows quad comparators 298 and 300 for providing limit signals at the output conductors 414, 416, 418 and 420, the purpose of which will be presently apparent. The voltages being compared are that at the conductor 111, which is the voltage of the cell, and the other voltage inputs at 422, 130, and 134 the origin of which will be presently apparent.

In addition, FIG. 7 shows the potentiometer 424 which is utilized to zero the sample and hold circuit of the device 54. Further, a conductor 426 is shown to receive an internally generated signal for controlling the converter range switch 218. Device "433" is a potentiometer adjusted to calibrate the analog to digital converter 55. Line "431" is the input and line "428" the output of a unity gain noninverting amplifier in device 55.

Figure 8:
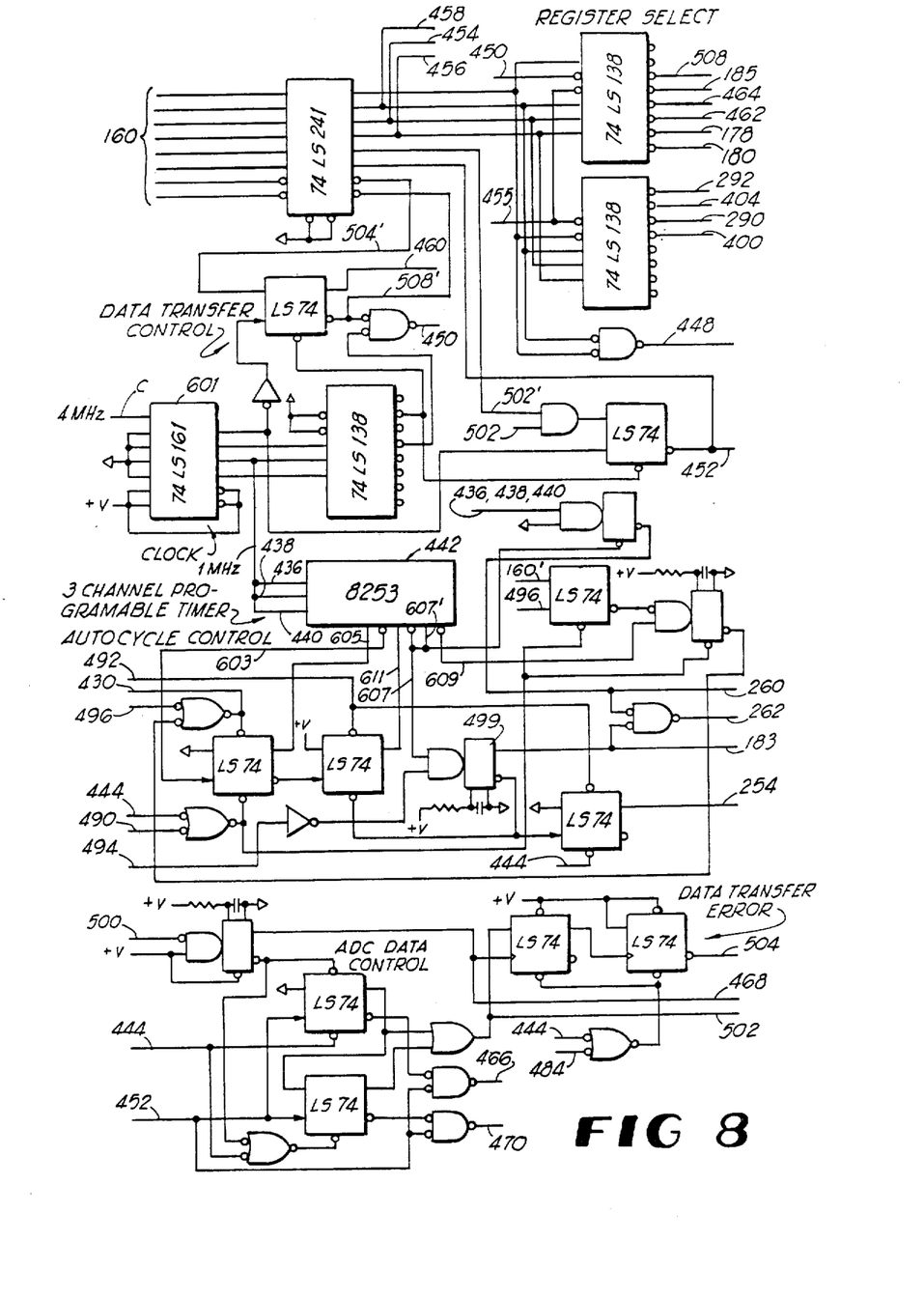
Figure 9:
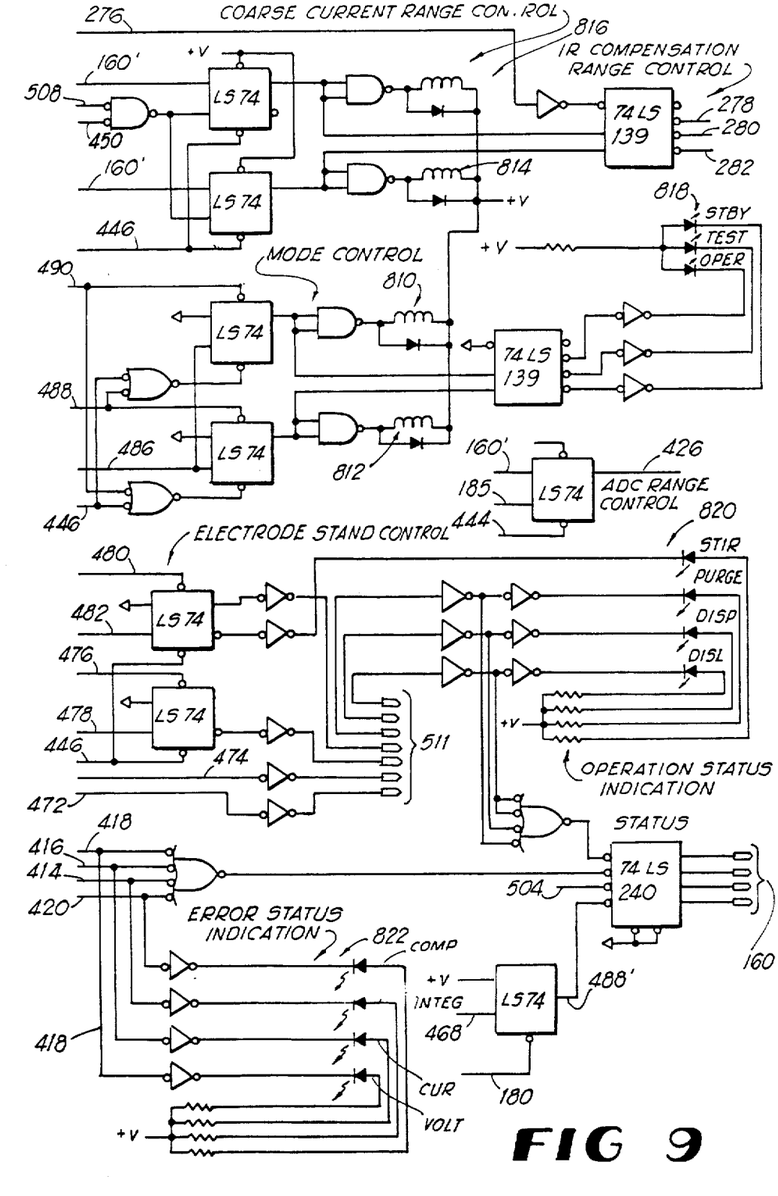

The control logic circuitry of FIG. 8, the control and status circuitry of FIG. 9, and the data bus and test control circuitry of FIG. 10 generate the internal signals mentioned above.

FIG. 10 illustrates the multiplexing/isolating device 104 (see FIG. 2) at the upper right-hand corner. This circuitry includes two multiplexers 413 and a control gate 415 which is controlled by the signals at 458 and 460. When the signals are present at 458 and 460, the multiplexers 413 permit the data from the data bus 160 to produce the signals 501, 503, 505, 507, 509, 511, 513, and 515 of the internal data bus 105. When either one or both of the signals is absent at 458 and 460, the multiplexers 413 are disabled so that the aforesaid signals are grounded as at 103. This effects the internal data bus grounding so as to the minimize background noise within the analog portion of the potentiostat.

Returning for a moment to FIG. 8, an internal crystal controlled clock (not shown) provides a four megahertz signal to the input conductor C of the clock device 601 which produces a one megahertz output signal at the conductor connected to the input conductors 436, 438 and 440 of the type 8253 device 442. The three 16-bit timers in the device 442 provide time delays during square wave of cycles (see FIG. 3). Each counter is operated as a digital one shot with the count decremented by the device 601 when the channel is enabled. When the count reaches zero, the channel is disabled and the potentiostat hardware starts the next timer channel. The first timer channel is output at the conductor 603 when enabled at the conductor 605. The second channel is output at the conductor 607 and the third channel is output at the conductor 609. The enabling input for the second timer channel is at the conductor 611 and the enabling input to the device 442 for the third timer channel is the output of the second timer channel as indicated at 607 prime.

At this point, it would be well to identify the designations and functions of the various control signals appearing in FIG. 8 as follows:

| 160' | Line of Data Bus | |
|---|---|---|
| 178 | LD EHB L | load high byte of DAC register |
| 180 | LD ELB L | load low byte of DAC register |
| 183 | ADC TRIG H | ADC trigger for data conversion |
| 185 | LD CHNL L | load analog mux channel |
| 254 | INT CUR H | interrupt cell current |
| 260 | INTEG EN H | integrate enable (high) |
| 262 | INTEG RST L | integrate reset |
| 290 | CZR SEL L | select current offset register |
| 292 | GCR SEL L | select gain control register |
| 400 | VZR SEL L | select voltage zero DAC |
| 404 | RU SEL L | select IR compensation register |
| 430 | ST+RST L | start and restart low |
| 444 | INIT L | initialize low |
| 448 | TMR SEL L | timer select low |
| 450 | WR STB L | write strobe low |
| 452 | RD L | read low |
| 454 | A1 | address list |
| 455 | RST H | reset high |
| 456 | A0 | address list |
| 458 | A2 | address list |
| 460 | WR H | write (high) |
| 462 | LD TST L | load test register low |
| 464 | EX CMD L | execute command low |
| 466 | RD ADC LB L | read ADC low byte |
| 468 | LD ADC DR H | load ADC data register high |
| 470 | RD ADC HB L | read ADC high byte |
| 484 | CLR ERR L | clear error |
| 490 | STOP L | stop command |
| 492 | CUR INT L | current interrupt low |
| 494 | CONVERT L | ADC convert command |
| 496 | START L | start command |
| 500 | ADC EOC L | ADC end of conversion low |
| 502 | DATA AVAIL H | data available high |
| 502' | RD RDY H | read ready high |
| 504 | DATA ERR L | data error low |
| 504' | WR RDY H | write ready high |
| 508 | LD CVC GR L | load compensation range control |
| 508' | WR L | write (low) |

At this time, the signals which do not appear above and which are designated in FIG. 9 are as follows:

| 276 | C OFF L | IR compensation off low |
|---|---|---|
| 278 | CR3L | IR compensation range 3 |
| 280 | CR2L | IR compensation range 2 |
| 282 | CR1L | IR compensation range 1 |
| 414 | INTEG LIM L | integration limit low |
| 416 | CUR LIM L | current limit low |
| 418 | VOLT LIM L | voltage limit low |
| 420 | COMP LIM L | compensation limit low |
| 426 | 20V SEL H | select 20V ADC range |
| 446 | BINIT L | buffered initialize |
| 472 | DISLODGE L | dislodge old drop |
| 474 | DISPENSE L | dispense 'new' drop |
| 476 | PURGE ON L | purge on |
| 478 | PURGE OFF L | purge off |
| 480 | STIR ON L | stir on |
| 482 | STIR OFF L | stir off |
| 486 | STBY L | standby mode |
| 488 | TEST L | test mode |
| 488' | DA FLG L | data available flag |
| 511 | signals to and from PARC 310 | |

The following signals, not listed above, appear in FIG. 10 as follows:

| 258 | TEST INTEG H | test integrator |
|---|---|---|
| 268 | IR TST1 L | IR test no. 1 |
| 270 | IR TST2 L | IR test no. 2 |
| 272 | IR TST3 L | IR test no. 3 |
| 274 | IR TST OFF L | IR test off |
| 284 | TEST IA H | test current amplifier |
| 406 | ZT3 L | zero test 3 low |
| 408 | ZT2 L | zero test 2 low |
| 410 | ZT1 L | zero test 1 low |
| 412 | ZT OFF L | zero test off low |
| 432 | UPDATE L | update cell voltage low |
| 434 | data output lines of ADC | |

From the above, it will appear that the data acquired by the instrument is the in the form of 12-bit data (11 bits plus sign) which is converted into sign extended, 16-bit format by the instrument and transferred to the computer in a low byte/high byte sequence. That is, as shown in FIG. 10, the two latches 162 and 164 receive data from the twelve lines 434, four of which are applied to the latch 162 and eight of which are applied to the latch 164. The control signal at 468 causes data to be transferred from the ADC 55 to latches 162 and 164. Then, the control signal at the conductor 466 causes the low byte information to be read from the latch 164 whereas the control signal at the conductor 470 allows the high byte to be read from the latch 162 to the computer over the data bus 160. Double buffering allows the ADC 55 to start a second conversion while data from the first conversion is being transferred to the computer. However, both bytes from the first conversion must be read by the computer prior to the end of the second conversion or data will be lost and the data error flag will be set in the potentiostat.

Any one of three methods can be used to transfer the data from the ADC 55 of the potentiostat to the computer. These methods are polled operation, input interrupts or direct memory access (DMA) transfer. The method used is a trade off between overall system performance and software complexity.

Figure 11:
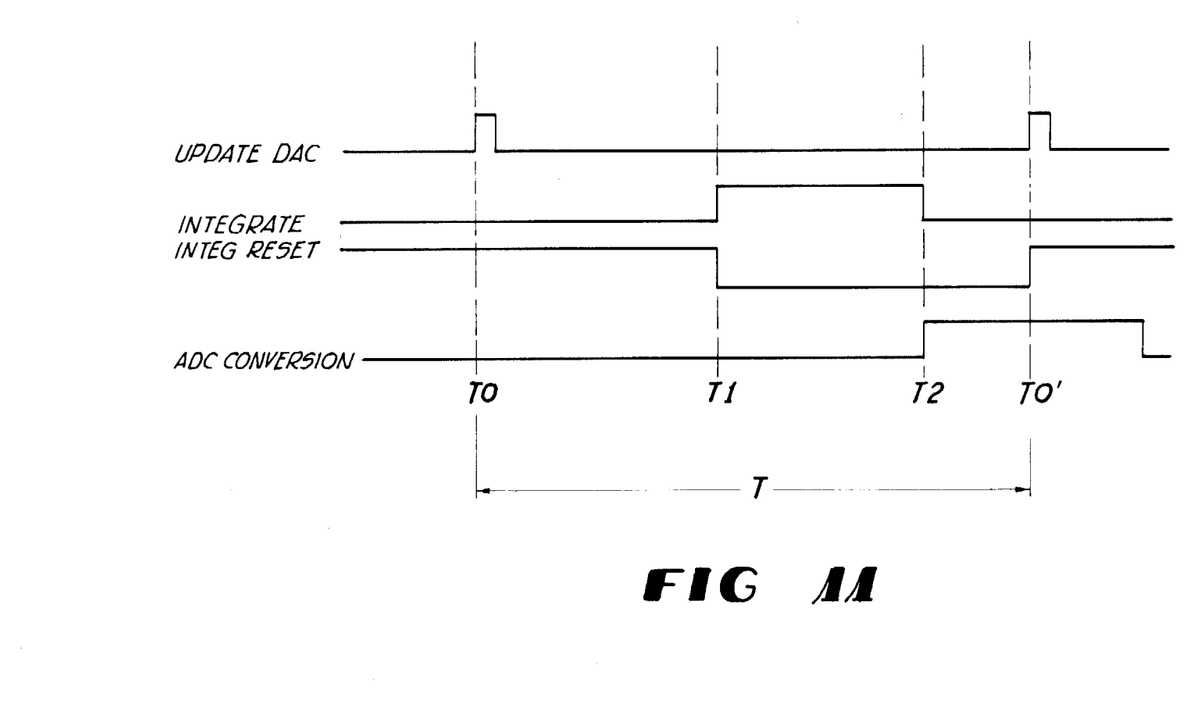
FIG. 11 is a timing diagram.

The timing sequence is also apparent from FIG. 8. The three 16-bit counters in the Intel 8253 are used to provide time delays during data acquisition cycles in either single or auto cyle operation. The timing sequence will be more readily apparent from the waveforms of FIG. 11. In referring to the timing diagram of FIG. 11, a cycle is initiated with a start command at time T0. The start command updates the output registers 172 and 176 with data loaded into the holding registers 170 and 174 and the timer channel 603 (FIG. 8) is started. The timer channel 603 determines the preintegration delay interval (T0 to T1) allowing the capacitive cell current to decay before integration starts. At time T1, the first timer times out which starts the second timer channel 607 and enables the cell current integration. The timer channel 607 determines the integration period T1 to T2. When the timer times out at time T2, the third timer channel 609 is started and an ADC conversion trigger is generated by the oneshot 499 in FIG. 8 at the conductor 183. The third timer channel determines the post integration delay (T2 to T0 prime) which must be of about 30 microseconds duration. If auto cycle mode is selected, a new conversion cycle is started (including DAC updating) when timer channel 609 times out at T0'. If single cycle mode is selected, a new start command must be issued to initiate the next conversion cycle.

The potentiostat has three operating modes, STANDBY, TEST, and OPERATE, which are selected by commands with the same names. The STANDBY mode is selected by default at power up or when a reset command is issued. In the STANDBY mode, the cell electrodes are disconnected through the switches previously described and the galvanostat circuit is closed by the relays 810 and 812 shown in FIG. 9. The relay 810 controls the switches 44, 76 and 92 in FIG. 2 whereas a relay 812 controls the switches 192, 194 and 196. The additional relays 814 and 816 respectively control the switches 96 and 98. The front panel of the instrument contains a number of light emitting diodes indicated generally by the reference characters 818, 820 and 822 in FIG. 9. FIG. 9 also shows a group of contacts 511 which are connected to the PARC and the status connections to certain of the conductors of the data bus 160.

A number of features of the invention are believed to be particularly unique. For example, the automatic measurement and adjustment of the DC current and the IR compensation is particularly valuable. Because of the technique of IR compensation, it is not necessary to select a potential at which the cell current is expected to be non-existent, but, rather the compensation technique is carried out in the presence of cell current. The rapidity of data collection is of particular significance. Because of the logic functions carried out in the potentiostat itself, the computer is released of substantial memory utilization and overhead time for performing these various functions and this, in turn, leads to the capability for allowing a display while the apparatus is actually collecting data, i.e., a real time display. A further very important feature of the invention is the isolation of the internal data bus of the potentiostat. This allows the very sensitive analog devices to operate in an environment of very low background noise and greatly increases the sensitivity of the instrument and accuracy of the interpretation of the data collected.

We claim:

1. A data acquisition system comprising computer means and a measuring and control instrument, said instrument including analog circuit means for measuring at least one variable analog function with high sensitivity, an internal data bus, digital-to-analog converter means connected to said analog circuit means and fed by said internal data bus for changing the condition of said analog circuit means in accord with digital input to said digital-to-analog converter means, analog-to-digital converter means connected to said analog circuit means for converting the variable analog function being measured to digital format, an active data bus connected with said analog-to-digital converter means for periodically acquiring data therefrom corresponding to the measured analog function, and means interfaced between said active data bus and said internal data bus for sequentially applying digital input from said computer means to said digital-to-analog converter means and for grounding the internal bus to allow the analog function to be measured without being degraded by digital noise.

2. A data acquisition system as defined in claim 1 including graphics display means connected to said computer means for displaying said digital format on a real time basis.

3. A data acquisition system as defined in claim 1 wherein said analog circuit means is effective to detect Faradaic current in a flow stream which has been differentially eluted.

4. A data acquisition system as defined in claim 1 further including logic means for controlling said measuring and control instrument without control input from said computer means after initialization.

5. A data acquisition system as defined in claim 4 wherein said meauring and control instrument further includes an electrochemical detector having an electrochemical cell.

6. A data acquisition system as defined in claim 1 wherein said measuring and control instrument further includes an electrochemical detector having an electrochemical cell.

7. A data acquisition system as defined in claim 6 wherein said digital-to-analog converter means controls voltage level to said electrochemical cell.

8. A data acquisition system as defined in claim 7 wherein said analog circuit means include means for effecting IR compensation.

9. A data acquisition system comprising computer means and a measuring and control instrument, said instrument including analog circuit means for measuring at least one variable analog function with high sensitivity, logic means for controlling the measuring and control instrument, and an internal data bus as an input to said analog circuit means; an active data bus connected to said computer means; input means for sequentially connecting said active data bus as an input to said internal data bus and for grounding said internal data bus for a time sufficient to allow measurement with high sensitivity; and output means for repetitiously converting said variable analog function to digital format and for connecting said digital format to said active data bus.

10. A data acquisition system as defined in claim 9 including graphics displaya means connected to said computer means for displaying said digital format on a real time basis.

11. A data acquisition system as defined in claim 9 wherein said logic means controls the rate at which said digital format is output to said active data bus whereby the computer means is relieved of the burden of necessary capacity for so doing.

12. A data acquisition system as defined in claim 9 including an internal data bus connected to said analog circuit means for conditioning said analog circuit means, and means controlled by said logic means for causing isolating and grounding of said internal data bus at least during times in which analog measurement is taking place so that analog measurement is not degraded by digital background noise which would otherwise be present.

13. A data acquisition system as defined in claim 12 wherein said analog circuit means is effective to detect Faradaic current in a flow stream which has been differentially eluted.

14. A data acquisition system as defined in claim 12 including digital to analog converter means connected to said internal data bus for changing the condition of said analog circuit means, said means for isolating including means for activating said internal data bus between periods of analog measurement to allow changing the condition of said analog circuit means.

15. A data acquisition system as defined in claim 14 wherein said analog circuit means is effective to detect Faradaic current in a flow stream which has been differentially eluted.

16. A data acquisition system as defined in claim 12 including graphics display means connected to said computer means for displaying said digital format on a real time basis.

17. A data acquisition system as defined in claim 16 wherein said analog circuit means is effective to detect Faradaic current in a flow stream which has been differentially eluted.

* * * * *